(12) United States Patent
Sun et al.

(10) Patent No.: US 8,501,987 B2
(45) Date of Patent: Aug. 6, 2013

(54) PROCESS FOR PRODUCTION OF GLYCOLIC ACID

(75) Inventors: Ying Sun, Liaoning (CN); Hua Wang, Liaoning (CN); Zhongmin Liu, Liaoning (CN); Martin Philip Atkins, Middlesex (GB)

(73) Assignees: Dalian Institute of Chemical Physics, Liaoning (CN); Chinese Academy of Sciences BP P.L.C., London (GB)

( * ) Notice: Subject to any disclaimer, the term of this patent is extended or adjusted under 35 U.S.C. 154(b) by 213 days.

(21) Appl. No.: 12/736,865

(22) PCT Filed: Mar. 16, 2009

(86) PCT No.: PCT/CN2009/000278
§ 371 (c)(1),
(2), (4) Date: Mar. 1, 2011

(87) PCT Pub. No.: WO2009/140850
PCT Pub. Date: Nov. 26, 2009

(65) Prior Publication Data
US 2011/0144388 A1    Jun. 16, 2011

(30) Foreign Application Priority Data
May 20, 2008 (WO) ................ PCT/CN2008/000970

(51) Int. Cl.
*C07C 27/06* (2006.01)
*C07C 51/10* (2006.01)

(52) U.S. Cl.
USPC .......................... 562/518; 568/861

(58) Field of Classification Search
USPC .................. 562/518; 568/864, 861
See application file for complete search history.

(56) References Cited

U.S. PATENT DOCUMENTS 4,087,470 A    5/1978  Suzuki
6,376,723 B2 *  4/2002  Drent et al. .................. 568/864

FOREIGN PATENT DOCUMENTS

DE        31 07 518 A1    12/1981

OTHER PUBLICATIONS

Reddy et al , Acidity constants of Supported Salts of Heteropoly Acids Using a Methodology Related to the Potentiometric Mass Tritration Technique, Mar. 2006, Journal of Solution Chemistry, vol. 35, No. 3 ,p. 407-423.*
International Search Report for PCT/CN2009/000278, mailed Jun. 11, 2009.
Written Opinion for PCT/CN2009/000278, mailed Jun. 11, 2009.

* cited by examiner

*Primary Examiner* — Taylor Victor Oh
(74) *Attorney, Agent, or Firm* — Nixon & Vanderhye (57) ABSTRACT

Process for producing glycolic acid by contacting carbon monoxide and formaldehyde, optionally in the presence of a solvent, with a catalyst including a solid acid. The solid acid is an acidic polyoxometalate compound insoluble in formaldehyde, glycolic acid and the optional solvent, and has a concentration of acid sites of greater than 60 µmol $g^{-1}$ on the external surface and/or a Hammett Acidity value of less than −12.8.

13 Claims, 4 Drawing Sheets

PROCESS FOR PRODUCTION OF GLYCOLIC ACID

This application is the U.S. national phase of International Application No. PCT/CN2009/000278, filed 16 Mar. 2009, which designated the U.S. and claims priority to International Application No. PCT/CN2009/000278, filed 20 May 2008, the entire contents of each of which are hereby incorporated by reference.

This invention relates to the production of glycolic acid, more specifically to the production of glycolic acid by carbonylation of formaldehyde.

BACKGROUND OF THE INVENTION

Ethylene glycol is a high volume and widely used chemical product, one of its main uses being in the production of polyester plastics and fibres. It is widely manufactured by the hydration of ethylene oxide, which itself is made by oxidation of ethylene.

An alternative method of producing ethylene glycol that avoids the need for an ethylene derivative, and consequently the need for a steam cracker to produce ethylene, is to use $C_1$ compounds as feedstock. Such processes include the reaction of carbon monoxide with formaldehyde, which results in the formation of glycolic acid, which can then be converted into ethylene glycol through processes such as hydrogenation, optionally after first being converted into a glycolic acid ester.

For example, He et al in Catalysis Today, 51 (1999), 127-134, describe the use of heteropolyacids as homogeneous catalysts for the carbonylation of formaldehyde or methyl formate.

U.S. Pat. No. 2,152,852 and U.S. Pat. No. 2,153,064 describe processes in which formaldehyde is contacted with an acidic catalyst and carbon monoxide, preferably with water, at elevated temperatures and pressures to produce glycolic acid. Inorganic and organic acids are stated to be suitable. In U.S. Pat. No. 2,153,064 pressures of 5 to 1500 atmospheres and temperatures of 50 to 350° C. are stated to be suitable.

WO 01/49644 describes a process in which formaldehyde or a derivative thereof is reacted with carbon monoxide in the presence of an acid catalyst and a sulphone solvent, the acid catalyst having a pKa value of below −1. Halogenated sulphonic acids are stated to be preferred, although strongly acidic ion-exchange resins are also stated to be suitable as heterogeneous catalysts.

SUMMARY OF THE INVENTION

There remains a need for an alternative process for producing glycolic acid from $C_1$ reactants.

According to a first aspect of the present invention, there is provided a process for producing glycolic acid comprising contacting carbon monoxide and formaldehyde optionally in the presence of a solvent with a catalyst comprising a solid acid, characterised by the solid acid being an acidic polyoxometalate compound insoluble in formaldehyde, glycolic acid and the optional solvent, and having a concentration of acid sites of greater than 60 µmol g$^{-1}$ on the external surface.

According to a second aspect of the present invention, there is provided a process for producing glycolic acid comprising contacting carbon monoxide and formaldehyde optionally in the presence of a solvent with a catalyst comprising a solid acid, characterised by the solid acid being an acidic polyoxometalate compound insoluble in formaldehyde, glycolic acid and the optional solvent, and having a Hammett Acidity ($H_0$) value of less than −12.8.

Polyoxometalate compounds comprise polyoxometalate anions, which are formed from a plurality of condensed metal-oxide species. With protons as counter-ions, they exhibit Brønsted acidity. There are a number of known polyoxometalate structures, for example the Wells-Dawson, Anderson and Keggin forms. Examples of acidic polyoxometalate compounds are heteropolyacids, which include silicotungstic acid, $H_4SiW_{12}O_{40}$, and phosphotungstic acid $H_3PW_{12}O_{40}$, both of which adopt the Keggin structure. Another example is iodomolybdic acid, $H_5Mo_6IO_{24}$, which adopts the Anderson structure. A further example is a different polymorph of phosphotungstic acid which adopts the Wells-Dawson structure, $H_6P_2W_{18}O_{62}$. Polyoxometalate structures and examples of compounds with such structures are described, for example, in Catalysis for Fine Chemical Synthesis, Volume 2: Catalysis by Polyoxometalates, edited by I. Kozhevnikov, Springer-Verlag, Berlin, 2003.

Such acids are generally highly soluble in water and polar organic solvents, such as alcohols, glycols, carboxylic acids, ketones and aldehydes. They can be supported on insoluble solids to produce heterogeneous catalysts, which can allow a high dispersion of heteropolyacid to be achieved. Typical supports include silica, alumina, aluminosilica, zirconia, ceria, titania, and carbon. However, in liquid phase reaction compositions there is a tendency for the polyoxometalate compounds to dissolve in the reaction mixture which, in the case of the present invention, comprises formaldehyde and glycolic acid, often in the presence of a solvent.

Polyoxometalate acids can be partially neutralised by other cations, for example ammonium, alkali-metal and alkaline-earth metal cations, some of which are insoluble in formaldehyde carbonylation reaction compositions. It has now been found that a particular class of insoluble acidic polyoxometalate salts are unexpectedly particularly active for the formaldehyde carbonylation reaction, in that their catalytic activity is not related to the number of protons associated with each polyoxometalate unit, but is instead related to the concentration of acid sites on the external surface of the insoluble acidic polyoxometalate compounds. In particular, it has been found that compounds with a concentration of acid sites on the external surface of greater than 60 µmol g$^{-1}$, more preferably greater than 65 µmol for example greater than 70 µmol g$^{-1}$, show surprisingly high activity.

It has been found that these materials have surprisingly low Hammett Acidity ($H_0$) values, typically below −12.8, and often lower than −13.5, for example lower than −13.8 or lower than −14.0.

It has also been found that the activity of the insoluble acidic polyoxometalate compounds appears to be related to the acid strength of the protons, as opposed to the number of protons. In particular, insoluble polyoxometalate acid compounds having Hammett acidity values ($H_0$) of less than −12.8 exhibit surprisingly enhanced catalytic activity. Preferably, the $H_0$ value of the insoluble polyoxometate acid is less than −13.5, more preferably less than −13.8 or −14.0.

In one embodiment of the invention, the solid insoluble polyoxometalate acid is a caesium salt of phosphotungstic acid represented by the formula $Cs_xH_{3-x}PW_{12}O_{40}$ where 2<x<3. The value of x is less than 3, as otherwise the phosphotungstic acid is completely neutralised. Where x is greater than 2, then the external surface acid site concentration is greater than 60 µmol g$^{-1}$. Where x is 2.5, the catalyst is particularly active, and the external surface acid site concentration is in excess of 75 µmol g$^{-1}$.

Other examples of insoluble polyoxometalate acids include potassium, barium and lead salts of the Keggin forms of phosphotungstic acid and silicotunstic acid, for example $K_{2.5}H_{0.5}PW_{12}O_{40}$ and $(NH_4)_{2.5}H_{0.5}PW_{12}O_{40}$, which have total surface areas of about 122 $m^2g^{-1}$ and 161 $m^2g^{-1}$ respectively.

The insoluble acidic polyoxometalate acid of the present invention typically has an external surface area of greater than 40 $m^2g^{-1}$, for example greater than 50 $m^2g^{-1}$, greater than 70 $m^2g^{-1}$ or greater than 100 $m^2g^{-1}$. The total surface area incorporates contributions from the external surface, and from micropores that exist within the structure, the micropores being defined herein as having a diameter of 2 nm or less. The external surface includes surfaces existing within mesopores, which are typically defined as pores with a diameter of greater than 2 nm. The total surface area is therefore the sum of the microporous surface area and the external surface area.

Surface areas are typically measured using adsorption techniques known to those in the art, for example nitrogen or argon adsorption. Thus, the measurement of surface area is a measurement of the surface of the solid accessible to the probe molecules such as nitrogen or argon. Calculating the extent of adsorption and desorption of probe molecules at various gas pressures of the probe molecule provides information not only on the surface area accessible to the probe molecules, but also on the type of porosity exhibited by the sample, for example the pore size distribution within the sample.

The total concentration of acid sites in the insoluble polyoxometalate acid is the number of acidic sites on the external and internal (i.e. microporous) surface of the solid. Preferably, the majority of the acid sites are on the external surface (which includes the surface within mesopores), i.e. the concentration of external surface acid sites is greater than 25% of the total concentration of surface acid sites, more preferably greater than 35% or 40% of the total concentration. Acid site concentration can be measured by techniques such as ammonia desorption.

The solid insoluble polyoxometalate acid can optionally be supported. This enables high dispersions of the polyoxometalate acid to be achieved, which can increase the catalyst turnover number, while its insoluble nature renders it resistant to leaching from the support. Typical supports include silica, alumina, aluminosilica, zirconia, ceria, titania, and carbon. Optionally, the support can have an ordered porous structure, as found in zeolites for example, such as those with the faujasite (FAU) structure exemplified by zeolite Y or dealuminated analogues such as USY (ultra-stable Y). Optionally, the support can comprise a mesoporous structure, such as found in the silicas or aluminosilicas SBA-15, MCM-41 or MCM-48. Mesoporous solids are typically defined as those which comprise pores with diameters of greater than 2 nm. An advantage associated with mesoporous supports is that they tend to have a high surface area, which allows a high degree of dispersion and/or loading of polyoxometalate, while the large pores associated with the structure ensure the high surface area is accessible to large reagents and catalysts with low restriction to diffusion for reagents and products, and also reduced potential for pore blocking.

Caesium salts of phosphotungstic acid can be made by adding a caesium salt, for example a halide, nitrate sulphate or hydroxide salt, to a solution of phosphotungstic acid. The caesium salts are typically insoluble in water or other polar solvents, for example alcohols, and hence can be readily separated by techniques such as filtration or centrifugation. The quantity of caesium salt required will depend on the desired value of x. In the case of x=2.5, for example, the synthesis is conducted so that 2.5 moles of caesium are added for each mole of phosphotungstic acid present in the solution. The phosphotungstic acid is preferably in the Keggin-form, i.e. with a heteropolyanion formula of $[PW_{12}O_{40}]^{3-}$.

Supported catalysts can be prepared by first impregnating the support with a soluble source of caesium, for example by evaporating to dryness a suspension of the support in a solution of a soluble caesium salt. The anions of the soluble caesium salt are preferably readily removable from the support, for example by being easily decomposed to volatile products or being easily removed through processes such as heating or calcination. Thus, salts such as hydroxide, nitrate or carbonate salts are preferred. In one embodiment, the support is calcined in air after impregnation with the soluble caesium salt to remove the anion. After impregnation with soluble caesium salt and optional further treatment such as calcination, the support can be contacted with a phosphotungstic acid solution. Typically, the solutions used in impregnating the caesium salt and phosphotungstic acid are aqueous, but organic solvents such as an alcohol, for example ethanol, n-propanol, iso-propanol or n-butanol, can also be used. The resulting catalyst is a solid, which can be separated by techniques such as filtration or centrifugation. Insoluble salts of other polyoxometalate acids can be produced in an analogous way.

When the catalyst is supported on a support, it is resistant to leaching, and even in the presence of solvent it can be reused several times without substantial sign of deactivation. This is in contrast to catalysts formed from soluble polyoxometalates, which tend to leach and hence deactivate with repeated use.

In the process of the present invention, the catalyst is contacted with carbon monoxide and formaldehyde, optionally in the presence of a solvent. The reaction temperature is typically in the range of from 50 to 400° C., for example in the range of from 100 to 250° C. Pressures are typically in the range of from 1 to 1000 bara (0.1 to 100 MPa), such as in the range of from 1 to 200 bara (0.1 to 20 MPa).

The process can be a liquid-phase process, in which the reaction composition comprises a solvent. In one embodiment, the solvent is a sulphone, for example 2,3,4,5-tetrahydrothiophene-1,1-dioxide, often known as sulfolane. Water can optionally be present, either as the solvent or mixed with one or more other solvents.

Liquid phase processes can be conducted in a continuous flow configuration, which in one embodiment involves feeding the components of the reaction composition, i.e. carbon monoxide, formaldehyde and optional solvent, either pre-mixed or separately, to a reactor comprising a fixed bed of catalyst, to produce a product composition which is continuously withdrawn from the reactor. Alternatively, the reaction can be conducted batch-wise, in which in one embodiment involves suspending and stirring a suspension of the catalyst in a liquid reaction composition comprising solvent and formaldehyde, with carbon monoxide being fed into the reactor under pressure. The resulting product composition can then be periodically removed from the reactor. Typically, any catalyst being removed from the reactor with the product stream is separated and fed back to the reactor to minimise catalyst loss.

The product composition comprises glycolic acid. The product composition can be treated to recover solvent and unreacted reactants, for example formaldehyde and carbon monoxide. This can be achieved by a variety of means. For example, formaldehyde and carbon monoxide can be recovered by flash separation and/or distillation.

Glycolic acid can be separated from the product composition by precipitation, for example by treatment with a salt such as a calcium salt, which converts the glycolic acid to an insoluble form which can then be separated by filtration, centrifugation or decantation. In another embodiment, the glycolic acid is treated with an alcohol, for example methanol or ethanol, to produce a glycolic acid ester which can be separated by distillation.

In one embodiment of the invention, the glycolic acid is converted to ethylene glycol. This is typically achieved by hydrogenation of the glycolic acid, or a process stream comprising glycolic acid. In a further embodiment, the glycolic acid is first converted to an ester, for example a methyl or ethyl ester by reaction with methanol or ethanol respectively, which can then be hydrogenated to recover the alcohol and produce ethylene glycol (often also referred to as mono-ethylene glycol or MEG). The hydrogenation is typically carried out catalytically, using a conventional hydrogenation catalyst for example palladium, platinum, rhodium, ruthenium, cobalt or nickel on a support such as carbon, silica or alumina. Other catalysts include mixed oxides of copper and one or more of magnesium, manganese, nickel, iron, cobalt, chromium, calcium, barium, strontium, potassium, caesium, zinc, cadmium and silver. Hydrogenation of glycolic acid or glycolic acid ester is described in U.S. Pat. No. 2,285,448.

The source of carbon monoxide reactant can be a pure source of carbon monoxide, optionally comprising small quantities of impurities such as one or more of light alkanes, carbon dioxide or hydrogen. Alternatively, the carbon monoxide source can be a component of a gaseous mixture, for example syngas which is a mixture of hydrogen and carbon monoxide.

Formaldehyde reactant can be generated in situ within the reactor. For example, in one embodiment of the invention, paraformaldehyde is used as a reactant. Paraformaldehyde is a polymer of formaldehyde, which reverts to monomeric formaldehyde in the presence of polar molecules, such as water or alcohol solvents.

BRIEF DESCRIPTION OF THE DRAWINGS

There now follow non-limiting examples of how the process of the present invention can be practiced. The examples are illustrated by the following Figures in which.

EXAMPLE 1

$Cs_{2.5}H_{0.5}PW_{12}O_{40}$ was prepared by adding 20 mL of 0.1M $Cs_2CO_3$ at a rate of 1 mL/min to 20 mL of a 0.08M solution of phosphotungstic acid hydrate under vigorous stirring for four hours at room temperature, resulting in the appearance of a white precipitate. The mixture was left to stand overnight at room temperature. The resulting white powder was isolated by evaporation under vacuum at 40° C. to produce a glass-like solid, which was ground to a powder and calcined under vacuum at 300° C. for 6 hours, before use in the catalytic experiments.

COMPARATIVE EXAMPLE 2

$Cs_2HPW_{12}O_{40}$ was prepared in the same way as Example 1, except that 12.7 mL of 0.1M $Cs_2CO_3$ and 15.9 mL of 0.08M phosphotungstic acid hydrate were used.

COMPARATIVE EXAMPLE 3

$Cs_{1.5}H_{1.5}PW_{12}O_{40}$ was prepared in the same way as Example 1, except that 9 mL of 0.2M $Cs_2CO_3$ and 30 mL of 0.08M phosphotungstic acid hydrate were used.

COMPARATIVE EXAMPLE 4

$CsH_2PW_{12}O_{40}$ was prepared in the same way as Example 1, except that 12 mL of 0.1M $Cs_2CO_3$ and 30 mL of 0.08M phosphotungstic acid hydrate were used.

COMPARATIVE EXAMPLE 5

$Cs_{0.5}H_{2.5}PW_{12}O_{40}$ was prepared in the same way as Example 1, except that 6 mL of 0.1M $Cs_2CO_3$ and 30 mL of 0.08M phosphotungstic acid hydrate were used.

COMPARATIVE EXAMPLE 6

$Cs_3PW_{12}O_{40}$ was prepared in the same way as Example 1, except that 27 mL of 0.1M $Cs_2CO_3$ and 22.5 mL of 0.08M phosphotungstic acid hydrate were used.

EXAMPLE 7

$Cs_{2.5}H_{0.5}PW_{12}O_{40}$ was supported on the mesoporous silica SBA-15 by suspending 3 g of SBA-15 in 30 mL of an aqueous solution comprising 0.09 mmol of $Cs_2CO_3$, and stirring the mixture overnight at room temperature. The suspension was then dried overnight at 110° C. The resulting solid was then calcined in air at 550° C. for 4 hours.

The solid was then impregnated with polyoxometalate using the incipient wetness technique, in this case by adding a solution of 0.072 mmol phosphotungstic acid dissolved in 15 mL 1-butanol, and stirring overnight at room temperature. The mixture was then dried at 110° C. for 12 hours, and calcined in air at 550° C. for 4 hours. The surface area of this $Cs_{2.5}H_{0.5}PW_{12}O_{40}$/SBA-15 material was 621 $m^2g^{-1}$.

COMPARATIVE EXAMPLE 8

$Cs_2HPW_{12}O_{40}$/SBA-15 was prepared using the same procedure as Example 7, except that 0.09 mmol phosphotungstic acid was dissolved in the 15 mL 1-butanol.

COMPARATIVE EXAMPLE 9

$CsH_2PW_{12}O_{40}$/SBA-15 was prepared using the same procedure as Example 7, except that 0.18 mmol phosphotungstic acid was dissolved in the 15 mL 1-butanol.

COMPARATIVE EXAMPLE 10

$Cs_{0.5}H_{2.5}PW_{12}O_{40}$/SBA-15 was prepared using the same procedure as Example 7, except that 0.36 mmol phosphotungstic acid was dissolved in the 15 mL 1-butanol.

COMPARATIVE EXAMPLE 11

$Cs_3PW_{12}O_{40}$/SBA-15 was prepared using the same procedure as Example 7, except that 0.06 mmol phosphotungstic acid was dissolved in the 15 mL 1-butanol.

EXAMPLE 12

$Cs_{2.5}H_{0.5}PW_{12}O_{40}$ supported on zeolite USY (a dealuminated form of zeolite Y) was prepared in an analogous way to the catalyst of Example 7, except that the SBA-15 was replaced with USY.

COMPARATIVE EXAMPLE 13

$H_3PW_{12}O_{40}$ supported on zeolite USY was prepared by the same method as Example 12, except that the support was not pre-loaded with caesium carbonate.

COMPARATIVE EXAMPLE 14

$Cs_{2.5}H_{0.5}PW_{12}O_{40}$ was prepared in an identical way to that of Example 1, except that 15 mL of 0.2M $Cs_2CO_3$ and 30 mL of 0.08M phosphotungstic acid hydrate were used and, after being left to age overnight, the sample was stirred in its supernatant solution for a second period of 3 hours before evaporation and calcination.

Before use, catalysts were dried in a glass tube reactor at 300° C. under vacuum for 6 hours. They were then allowed to cool and were held in dry nitrogen until required.

Catalysts were tested in a batch reaction, in which 0.2 g paraformaldehyde, 25 g (20 mL) sulfolane, 0.12 g water and 1 g catalyst was added to a 100 mL stainless steel autoclave fitted with a Teflon™ liner. The autoclave was purged with CO three times, before finally being filled with CO to a pressure of 4.0 MPa (40 bara) and heated slowly to reaction temperature of 120° C. Reaction was continued for 4 hours. The pressure in the autoclave at the reaction temperature is estimated as 5.4 MPa (54 bara).

The resulting suspension was filtered to remove catalyst, and the reaction product filtrate was treated with 2 g methanol at 70° C. for 2 hours to convert any glycolic acid to the corresponding methyl ester before the filtrate was analysed by gas chromatography (GC). This is required, as glycolic acid can decompose under GC conditions.

Table 1 lists physical data for different caesium salts of phosphotungstic acid, and compares this with catalytic activity. Table 2 lists surface acid concentrations of caesium salts of phosphotungstic acid.

Hammett Acidity ($H_0$) values were calculated using eight indicators with known pKa values, ranging from −3.3 to −14.52. The indicators used and their pKa values were: 2,4-dinitrofluorobenzene (−14.52), 2,4-dinitrotoluene (−13.7), m-nitrochlorobenzene (−13.16), p-nitrochlorobenzene (−12.7), p-nitrotoluene (−11.35), anthraquinone (−8.2), benzalacetophenone (−5.6), dicinnamalacetone (−3.0). The $H_0$ values quoted in Table 1 correspond to the pKa value of the indicator with lowest pKa value (i.e. most negative) that could be protonated by the sample. Protonation of the indicator was detectable by a colour change of the indicator.

From Tables 1 and 2, it can be seen that Example 1 (x=2.5) has a remarkably high surface area, external surface area and external surface acid site concentration. These properties correlate with a very high acidity (low $H_0$ value), and high catalytic activity in terms of glycolic acid yield.

TABLE 1

Physical data and catalytic activities of $Cs_xH_{3-x}PW_{12}O_{40}$.

| | | Surface Area (m²/g) | | | Acid Strength | Glycolic Acid |
|---|---|---|---|---|---|---|
| x | Example | Micropore | External | Total | ($H_0$) | Yield (%) |
| 0.48 | 5<sup>a</sup> | — | — | 2 | −12.7 | 25.6 |
| 1.0 | 4<sup>a</sup> | — | — | 2 | −12.7 | 36.5 |
| 1.48 | 3<sup>a</sup> | — | — | 3 | −11.35 | |
| 1.95 | 2<sup>a</sup> | 27 | 37 | 64 | −11.35 | 40 |
| 2.49 | 1 | 13 | 120 | 133 | −14.52 | 73.5 |
| 2.50 | 14<sup>a</sup> | 117 | 17 | 134 | −11.35 | |
| 2.97 | 6<sup>a</sup> | 15 | 139 | 152 | −3.0 | 1.2 |

<sup>a</sup>Comparative Example

TABLE 2

Proton Concentrations of $Cs_xH_{3-x}PW_{12}O_{40}$

| x | Example | Total Proton Concentration (μmol/g) | External Proton Concentration (μmol/g) |
|---|---|---|---|
| 0 | — | 1041.6 | 20.6 |
| 0.5 | 5<sup>a</sup> | 856.1 | 6.9 |
| 1.0 | 4<sup>a</sup> | 664.0 | 5.5 |
| 2.0 | 2<sup>a</sup> | 318.1 | 53.3 |
| 2.5 | 1 | 159.0 | 84.0 |
| 3.0 | 6<sup>a</sup> | 9.2 | 5.7 |

<sup>a</sup>Comparative Example

Comparing Comparative Example 14 with Example 1 (both having x=2.5), the samples have very different activities and Hammett acidities. It is apparent that the synthetic procedure has created differences in the proportion of surface area existing within micropores, which has surprising consequences inter alia on the Hammett Acidity and the catalytic activity.

In the Figures, labels 1 to 14 correspond to Examples and Comparative Examples 1 to 14 respectively.

Figure 1:
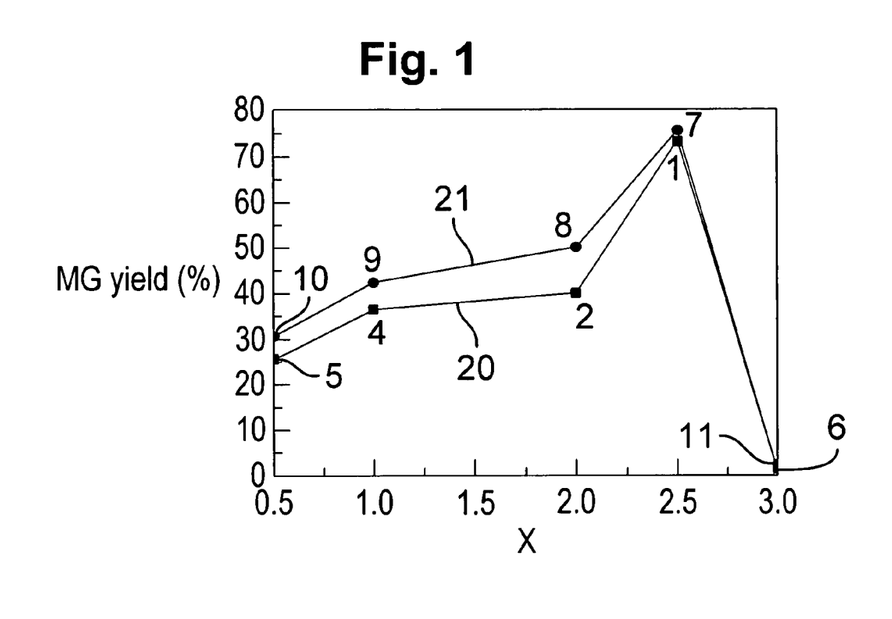
FIG. 1 is a graph showing the yields of glycolic acid produced with supported and unsupported $Cs_xH_{3-x}PW_{12}O_{40}$ catalysts.

FIG. 1 shows plots of the yield of methyl glycolate in the presence of $Cs_xH_{3-x}PW_{12}O_{40}$ at various x values, 20, and also methyl glycolate yields for the corresponding compounds supported on the silica SBA-15, 21. The results demonstrate that activity of the catalysts follows the same trend when caesium salts of phosphotungstic acid ($Cs_xH_{3-x}PW_{12}O_{40}$) are supported, in this case on a mesoporous silica SBA-15. Supporting the catalyst on a support improves dispersion of the active catalyst, which can improve the catalytic activity per polyoxometalate unit. FIG. 1 additionally highlights the sharp increase in activity where x is between 2 and 3.

Figure 2:
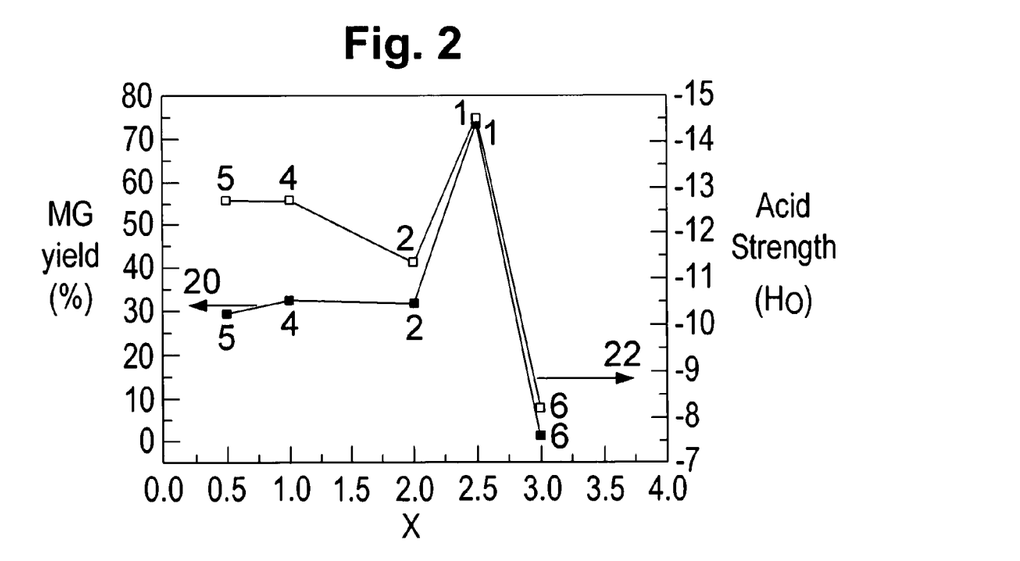
FIG. 2 is a graph showing the yields of glycolic acid produced and the Hammett acidity value of $Cs_xH_{3-x}PW_{12}O_{40}$ catalysts.

FIG. 2 shows the glycolic acid yield, 20, and the Hammett Acidity value ($H_0$), 22, as a function of x (i.e. caesium content) for the unsupported caesium salts of phosphotunstic acid ($Cs_xH_{3-x}PW_{12}O_{40}$). Phosphotungstic acid is identified as 15 These results also highlight the sharp increase in activity where x is between 2 and 3, which also correlates with a sharp decrease in the Hammett Acidity value.

Figure 3:
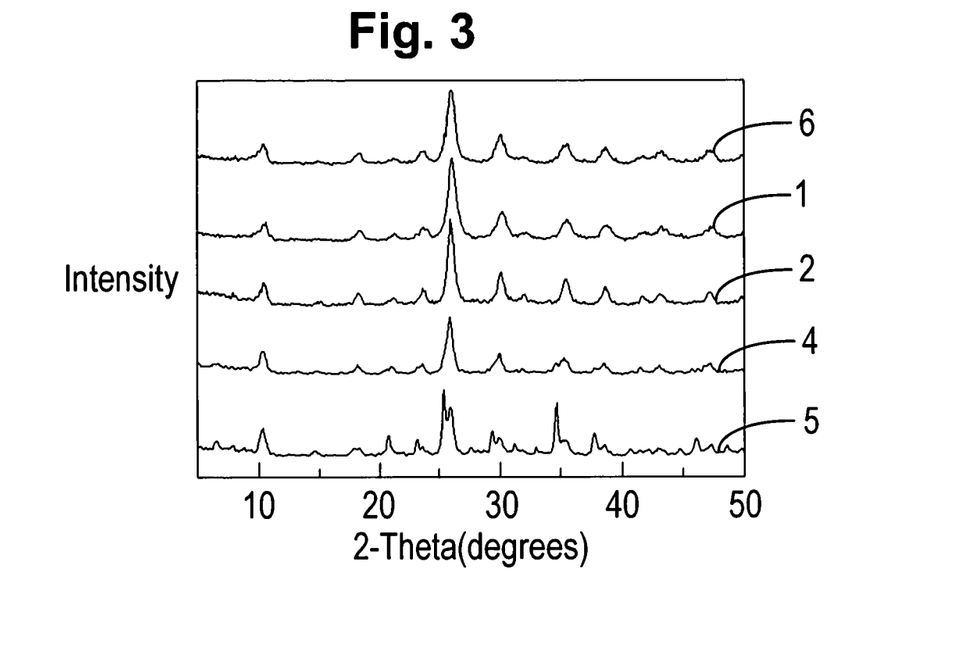
FIG. 3 is a series of X-Ray Diffraction patterns comparing the crystal structures of the different caesium salts of phosphotungstic acid.
Figure 4:
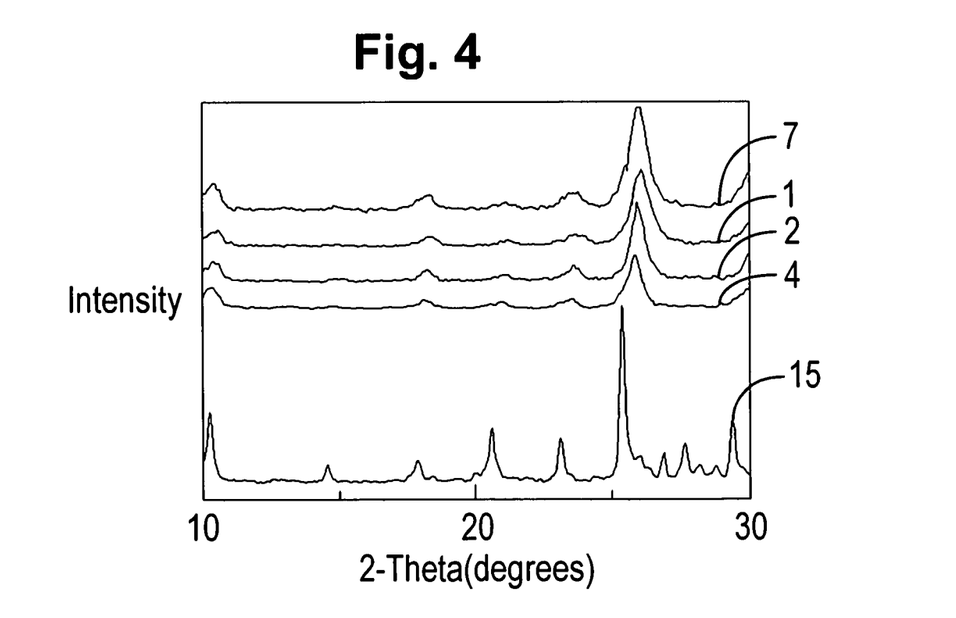
FIG. 4 is a series of X-Ray Diffraction patterns comparing the crystal structures of the supported and unsupported caesium salts of phosphotungstic acid.

FIGS. 3 and 4 show the X-ray diffraction (XRD) patterns of phosphotungstic acid, 15, some caesium salts of phosphotungstic acid, 1, 2, 4, 5 and 6, and an SBA-15-supported caesium salt, 7. It can be seen that the overall structure for the materials is generally the same, except that the peaks are broader when caesium is present, indicating lower long-range order, and are also shifted to higher 2θ values, indicating that the unit cell dimensions contract in the presence of caesium. The crystal structure of the supported polyoxometalate does not appear to change when supported on the silica SBA-15.

In FIG. 4, the x=0.5 salt appears to be a mixture of two phases, one corresponding to phosphotungstic acid (i.e. x=0), and one corresponding to the other caesium salts with higher x values. There is also some evidence of such a mixture in the x=1 salt, but to a much lesser extent, the predominant phase being associated with the structure of the salts with higher x values.

Thus, from XRD, there does not appear to be any significant change in long-range crystal structure that could explain the unexpectedly enhanced activity of the x=2.5 salt compared, for example, to salts with x values of lower value, and it is therefore not obvious why the x=2.5 salt has such a comparatively high surface area, external surface area, external acid site concentration or such a low (i.e. more negative) $H_0$ value.

Table 3 compares the activity of $Cs_{2.5}PW_{12}O_{40}$ and $H_3PW_{12}O_{40}$ supported on zeolite USY after a number of re-uses. It is clear from the retention of glycolic acid yield for each use that the caesium salt of phosphotungstic acid retains its activity between each re-use. From Table 4, which shows the extent of polyoxometalate loss from the support between each use, the loss of glycolic acid yield with the supported phosphotungstic acid catalyst correlates with the extent of leaching of phosphotungstic acid from the support.

TABLE 3

Glycolic acid yields for re-used catalysts.

| | | Glycolic Acid Yield (%) | | | | |
|---|---|---|---|---|---|---|
| Catalyst | Example | 1 | 2 | 3 | 4 | 5 |
| 30% $Cs_{2.5}H_{0.5}PW$/USY | 12 | 75.6 | 74.8 | 75.2 | 73.5 | 74.1 |
| 30% $H_3PW_{12}O_{40}$/USY | 13[a] | 79.8 | 21.7 | 8.6 | 2.7 | 1.2 |

[a]Comparative Example

TABLE 4

Cumulative loss of polyoxometalate from the support over repeated catalyst use.

| | | Polyoxometalate Loss (%)[b] | | | | |
|---|---|---|---|---|---|---|
| Catalyst | Example | 1 | 2 | 3 | 4 | 5 |
| 30% $Cs_{2.5}H_{0.5}PW$/USY | 12 | 0 | 0.1 | 0.1 | 0.2 | 0.2 |
| 30% $H_3PW_{12}O_{40}$/USY | 13[a] | 79.1 | 85.8 | 87.0 | 87.5 | 87.8 |

[a]Comparative Example

Figure 5:
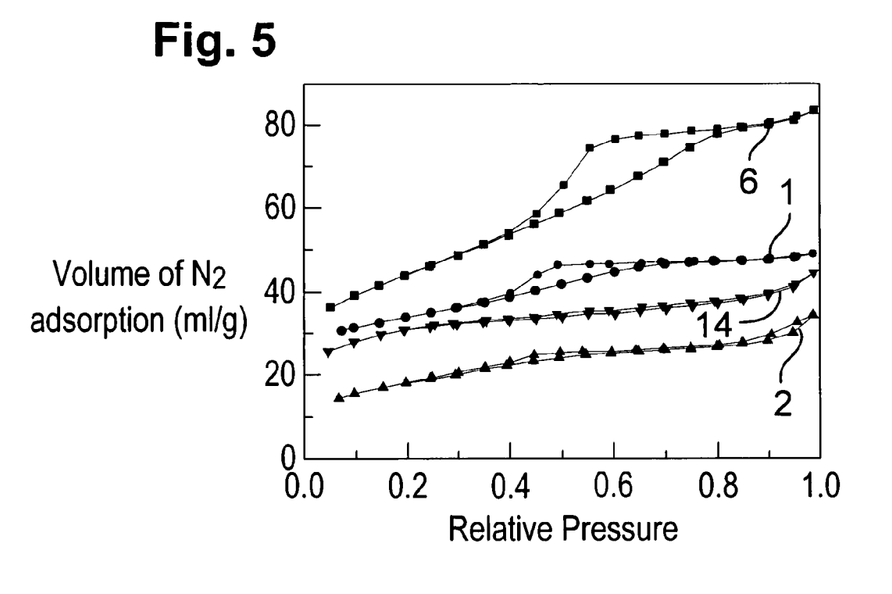
FIG. 5 is a series of nitrogen adsorption/desorption isotherms, comparing porosity characteristics of unsupported caesium salts of phosphotungstic acid.

FIG. 5 shows nitrogen adsorption/desorption isotherms for some of the unsupported caesium phosphotungstate materials, of Examples 1, 2, 6, and 14, corresponding to x=2.5, 2, 3, and 2.5 respectively. The isotherms for Examples 1 and 6, particularly the non-coincidence of the adsorption/desorption curves are very characteristic of mesoporosity. This also highlights a difference between Examples 1 and 14, which compositionally are similar but structurally are different in that Example 14 exhibits less mesoporosity and a higher degree of microporosity.

Figure 6:
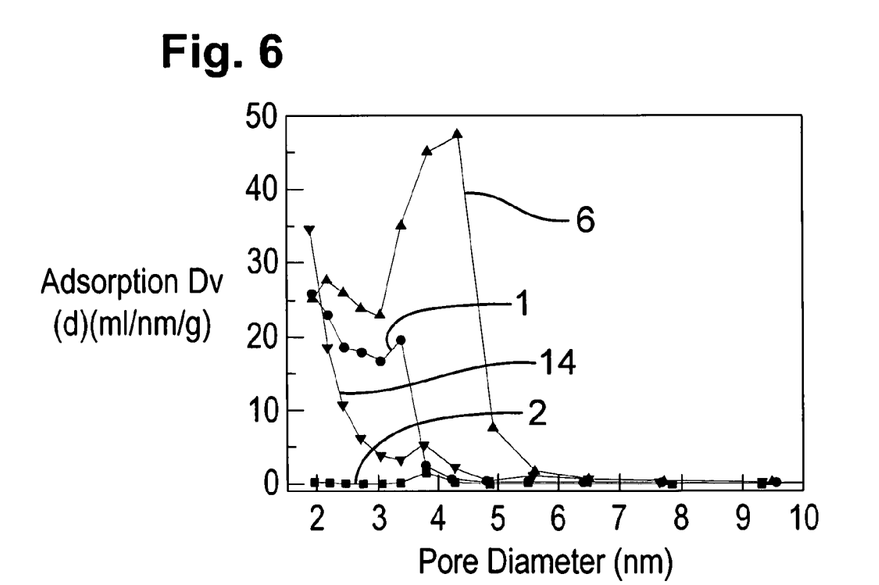
FIG. 6 shows pore size distributions calculated from the nitrogen adsorption/desorption isotherms in FIG. 5.

This is highlighted in the pore size distribution plots shown in FIG. 6, which were calculated from the nitrogen adsorption/desorption isotherms of FIG. 5. Example 1 has a greater proportion of its pores with diameters of 2 nm or more, compared to Example 14.

Figure 7:
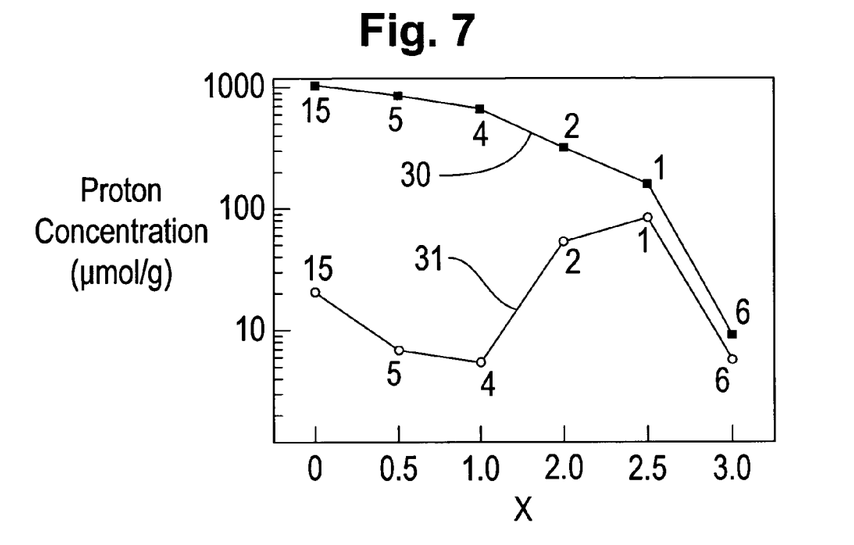
FIG. 7 is a graph showing the relationship between total surface and external surface acid site concentration for unsupported caesium salts of phosphotungstic acid.

FIG. 7 shows the relationship between x and both the total acid amount and the external concentration of acid sites of the caesium salts of phosphotungstic acid for Examples 1, 2, 4, 5 and 6, as tabulated in Table 2. The filled square data points, 30, represent the total surface area, and the open circular data points, 31, represent the external surface area.

Figure 8:
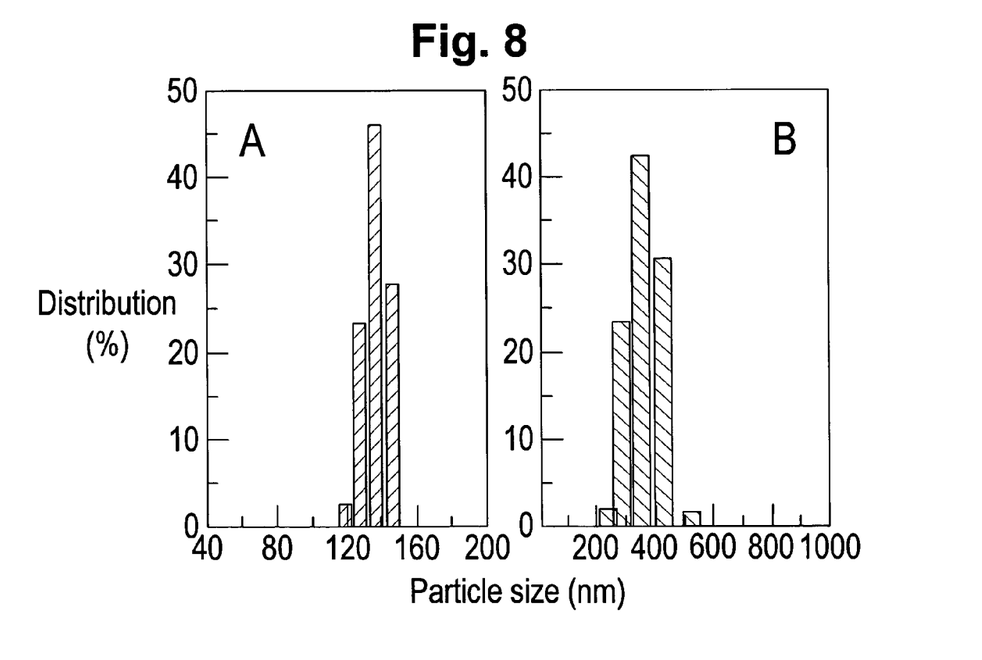
FIG. 8 shows particle size distributions of $Cs_{2.5}H_{0.5}PW_{12}O_{40}$ prepared by two different synthetic routes.

FIG. 8 shows the differences in particle size distribution between Examples 1 (plot A) and Example 14 (plot B). For each sample, the x value is the same, but the method of synthesis was different. The larger particle sizes of Example 14 are consistent with it having a lower external surface area and lower concentration of external acid sites compared to Example 1, where the average particle size is lower.

The invention claimed is:

1. A process for producing glycolic acid comprising contacting carbon monoxide and formaldehyde, optionally in the presence of a solvent, with a catalyst comprising a solid acid, wherein the solid acid is an acidic polyoxometalate compound insoluble in formaldehyde, glycolic acid and the optional solvent, and having a concentration of acid sites of greater than 60 µmol g$^{-1}$ on the external surface and/or a Hammett Acidity value of less than −12.8.

2. A process as claimed in claim 1, in which the $H_0$ value of the acidic polyoxometalate compound is less than −14.0.

3. A process as claimed in claim 1, in which the total surface area of the acidic polyoxometalate compound is greater than 70 m$^2$ g$^{-1}$.

4. A process as claimed in claim 1, in which the external surface area of the acidic polyoxometalate compound is greater than 40 m$^2$ g$^{-1}$.

5. A process as claimed in claim 1, in which the acidic polyoxometalate compound is a cesium salt of the Keggin form of phosphotungstic acid with a formula of $Cs_xH_{3-x}PW_{12}O_{40}$, where 2<x<3.

6. A process as claimed in claim 5, in which x=2.5.

7. A process as claimed in claim 1, in which the solid acid is supported.

8. A process as claimed in claim 1, in which the process is a liquid phase process, the process being carried out in the presence of a solvent.

9. A process as claimed in claim 8, in which the solvent is a sulphone or a combination of a sulphone and water.

10. A process as claimed in claim 1, in which the reaction temperature is in the range of from 50 to 400° C., and the pressure is in the range of from 1 to 1000 bara (0.1 to 100 MPa).

11. A process as claimed in claim 1 in which the glycolic acid product is converted into ethylene glycol.

12. A process as claimed in claim 11, in which the glycolic acid product is converted into ethylene glycol through hydrogenation.

13. A process as claimed in claim 12, in which the glycolic acid is first converted to an ester by reaction with an alcohol before being hydrogenated to ethylene glycol.

* * * * *